United States Patent
Ponaka et al.

(10) Patent No.: US 8,900,525 B2
(45) Date of Patent: *Dec. 2, 2014

(54) PREPARATION OF GLASSIFIED BIOLOGICAL REAGENTS

(75) Inventors: Reddy Ponaka, Dayton, NJ (US); Joseph W. Farchaus, Bloomsbury, NJ (US); Michael D. Pierce, Flemington, NJ (US)

(73) Assignee: GE Healthcare Bio-Sciences Corp., Piscataway, NJ (US)

( * ) Notice: Subject to any disclaimer, the term of this patent is extended or adjusted under 35 U.S.C. 154(b) by 687 days.

This patent is subject to a terminal disclaimer.

(21) Appl. No.: 12/439,274

(22) PCT Filed: Sep. 13, 2007

(86) PCT No.: PCT/US2007/078376
§ 371 (c)(1),
(2), (4) Date: Feb. 27, 2009

(87) PCT Pub. No.: WO2008/036544
PCT Pub. Date: Mar. 27, 2008

(65) Prior Publication Data
US 2009/0325263 A1    Dec. 31, 2009

Related U.S. Application Data

(60) Provisional application No. 60/845,307, filed on Sep. 18, 2006, provisional application No. 60/887,364, filed on Jan. 31, 2007.

(51) Int. Cl.
*G01N 31/22*    (2006.01)

(52) U.S. Cl.
USPC .......................................... 422/417; 422/500

(58) Field of Classification Search
USPC ................................. 422/417, 500
See application file for complete search history.

(56) References Cited

U.S. PATENT DOCUMENTS

| | | | |
|---|---|---|---|
| 3,300,474 A | 1/1967 | Flodin et al. | |
| 4,498,782 A * | 2/1985 | Proctor et al. | 356/436 |
| 5,053,332 A * | 10/1991 | Cook et al. | 435/178 |
| 5,098,893 A * | 3/1992 | Franks et al. | 514/54 |
| 5,200,399 A | 4/1993 | Wettlaufer et al. | |
| 5,240,843 A | 8/1993 | Gibson et al. | |
| 5,565,318 A | 10/1996 | Walker et al. | |
| 5,593,824 A * | 1/1997 | Treml et al. | 435/4 |
| 5,962,244 A * | 10/1999 | Lynch et al. | 435/15 |
| 6,485,913 B1 * | 11/2002 | Becker et al. | 506/13 |
| 6,977,722 B2 * | 12/2005 | Wohlstadter et al. | 356/246 |
| 7,048,915 B2 | 5/2006 | Kuroita et al. | |
| 7,303,869 B2 * | 12/2007 | Stevens et al. | 435/6.1 |
| 2003/0119042 A1 * | 6/2003 | Franco De Sarabia Rosado et al. | 435/6 |
| 2006/0172928 A1 | 8/2006 | Klapproth | |
| 2007/0190163 A1 * | 8/2007 | Malaknov et al. | 424/499 |

FOREIGN PATENT DOCUMENTS

| | | | |
|---|---|---|---|
| EP | 383569 A | * | 8/1990 |
| EP | 0 383 569 | | 5/1994 |
| EP | 1 452 099 | | 9/2004 |
| WO | WO 96/32497 | | 10/1996 |

OTHER PUBLICATIONS

BD Sprint Advantage® 96 Plate (http://www.clontech.com/clontech/archive/JUL02UPD/pdf/Sprint 96 Plate.pdf; Clonetechniques. Jul. 2002).*
Aaron Equipment Company (2013) from http://www.aaronequipment.com/usedequipment/dryers-drying-equipment.*
Sprint Advantage 96 Plate, Clone Technique, Jul. 2002, http://clontech.takara-bio.co.jp.
Early, J., et al., DNA Sequence—Journal of DNA Sequencing and Mapping, vol. 4, 1993, pp. 79-85.
Colaco, et.al. Biotechnology vol. 10, 1992, pp. 1007-1111.
Ortlepp, et.al. Biotechniques vol. 7, No. 10, 1989 pp. 1110-1115.
Ramanujam, et.al., Biotechniques, vol. 14, No. 3, 1993.
Overcashier, et.al. Journal of Pharmaceutical Sciences, vol. 88, No. 7, 1999 pp. 688-695.

* cited by examiner

*Primary Examiner* — Ardin Marschel

(57) ABSTRACT

The invention related to a method of making a dried reagent preparation, comprising the steps of: providing an aqueous solution of at least one buffered biological reagent; mixing a glass forming filler material with the buffered reagent solution to form a mixture wherein the concentration of the filler material is sufficient to facilitate formation of a glassy, porous composition; dispensing the mixture in the form of substantially uniform droplets into wells of a multi-well container, wherein a single droplet is dispensed into each well; drying the droplets in the container to form the reagent preparation. The reagent preparation is water soluble and has a Tg sufficient for room temperature stability.

21 Claims, 11 Drawing Sheets

| Quantity | puRe Taq 40°C | | puReTaq RT | | Current invention 40°C | | Current invention RT | |
| --- | --- | --- | --- | --- | --- | --- | --- | --- |
| | A | B | A | B | A | B | A | B |
| 10^7 | 9.65 | 9.89 | 9.67 | 9.69 | 0 | 9.78 | 9.85 | 10.05 |
| 10^6 | 12.81 | 12.86 | 12.73 | 12.98 | 12.78 | 12.65 | 13.23 | 13.13 |
| 10^5 | 16.58 | 16.46 | 16.26 | 16.11 | 16.43 | 16.10 | 16.60 | 16.43 |
| 10^4 | 20.18 | 20.14 | 19.49 | 19.73 | 19.57 | 19.53 | 20.50 | 20.07 |
| 10^3 | 23.46 | 23.37 | 23.10 | 23.23 | 23.07 | 23.15 | 23.70 | 23.72 |
| NTC | 35.11 | 35.17 | 35.04 | 34.51 | 34.01 | 32.49 | 33.35 | 33.70 |
| R2 Value | 0.99 | 0.99 | 0.99 | 0.99 | 0.99 | 0.99 | 0.99 | 0.99 |
| Slope | -3.66 | -3.50 | -3.50 | -3.50 | -3.40 | -3.50 | -3.60 | -3.50 |
| % PCR efficiecy | 87.60 | 93.07 | 93.07 | 93.07 | 96.84 | 93.07 | 89.57 | 93.07 |

FIGURE 8

PREPARATION OF GLASSIFIED BIOLOGICAL REAGENTS

CROSS REFERENCE TO RELATED APPLICATIONS

This application is a filing under 35 U.S.C. §371 and claims priority to international patent application number PCT/US2007/078376 filed Sep. 13, 2007, published on Mar. 27, 2008, as WO 2008/036544, which claims priority to U.S. provisional patent application Nos. 60/845,307 filed Sep. 18, 2006 and 60/887,364 filed Jan. 31, 2007; the entire disclosures of which are incorporated herein by reference in their entireties.

FIELD OF THE INVENTION

This invention relates to the long-term storage of biological materials and reagents in a glassy, porous state. In particular, it relates to methods of making these materials and reagents using a multi-well plate and the storage thereof.

BACKGROUND OF THE INVENTION

Few biologically active materials are sufficiently stable so that they can be isolated, purified, and then stored in solution at room temperature. Typically, biological reagents are stored in a glycerol solution which is maintained at temperatures of 4° C., −20° C., or −70° C. They may be stored in bulk and then combined with other reagents before use.

In preparing reagents for convenient and efficient testing of biological samples, it is frequently important to obtain dry chemical blends in uniform, discreet amounts. One type of carrier or filler which has been used to stabilize biological reagents is glass-forming filler materials. The biological reagent solutions are incorporated into the glass-forming filler materials (which are water soluble or a water-swellable substance). They are then dried to produce a glassy composition which immobilizes and stabilizes the biological reagent. For examples of glass-forming filler materials for stabilizing biological reagents see U.S. Pat. Nos. 5,098,893; 5,200,399 and 5,240,843.

Carbohydrates such as glucose, sucrose, maltose or maltotriose are an important group of glass-forming substances. Other polyhydroxy compounds can be used such as carbohydrate derivatives like sorbitol and chemically modified carbohydrates. Another important class of glass-forming substances are synthetic polymers such as polyvinyl pyrrolidone, polyacrylamide, or polyethyleneimine.

Further examples of glass-forming substances include sugar copolymers such as those sold by GE Healthcare under the registered trademark FICOLL™. FICOLL™ has molecular weights of 5,000 to 1,000,000 and contains sucrose residues linked through ether bridges to bifunctional groups (U.S. Pat. No. 3,300,474). Such groups may be an alkylene of 2, 3 or more carbon atoms but not normally more than 10 carbon atoms. The bifunctional groups serve to connect sugar residues together. These polymers may, for example, be made by reaction of sugar with a halohydrin or bis-epoxy compound.

Stabilized biological materials in a glassy matrix of carbohydrate polymers, can be prepared, either by freeze-drying (Treml et al. U.S. Pat. No. 5,593,824; Franks and Hatley U.S. Pat. No. 5,098,893) or by vacuum drying (Walker et al. U.S. Pat. No. 5,565,318). These water-soluble reagents are convenient to use for complex molecular biology applications. This approach is particularly useful for reagent systems composed of enzymes, nucleotides and other components dispensed in single-use aliquots. Reconstitution of the glassy matrix delivers buffered enzymes for applications including DNA amplifications and DNA sequencing.

There are currently a number of dried molecular biology products on the market. However, some of these are made by a process that is rather cumbersome, and involves extensive manual work. Other products require refrigeration when dried. There is a need for an improved process for the generation of ambient temperature dried reagents.

SUMMARY OF THE INVENTION

In a first aspect of the invention, it is provided a method of making a dried reagent preparation. The method comprises the steps of: providing an aqueous solution of at least one buffered biological reagent; mixing a glass forming filler material with the buffered reagent solution to form a mixture wherein the concentration of the filler material is sufficient to facilitate formation of a glassy, porous composition; dispensing a predetermined amount of the mixture into wells of a multi-well container; drying the mixture in the container to form the dried reagent preparation; wherein the reagent preparation is water soluble and has a Tg sufficient for room temperature stability. The mixture is preferably a homogeneous solution.

In one embodiment of the invention, the dried reagent preparation is collected into a reagent bottle for prolonged room temperature storage.

In another embodiment of the invention, the dried reagents are stored in the multi-well container, with the top of the container sealed with a sealing tape for prolonged storage. Optionally, the sealing tape is heat-activated.

The multi-well container according to the invention can be a silica mould or a polystyrene plate. When the multi-well container is a polystyrene plate, the invention further comprises placing the polystyrene plate on a metal mould prior to lyophilizing, so that the outside wall of each well of the polystyrene plate is in close contact with a well of said metal mould for efficient heat transfer. We discovered that this improves the drying process and produces dried reagents of improved integrity.

In another aspect of the invention, the present invention provides a dried biological reagent composition made according to the above methods.

The reagent composition made according to the invention is water soluble and has a $T_g$ sufficient for room temperature stability. Preferably, the reagent composition has structural integrity.

The biological reagent composition is capable of completely dissolving in 25 µl of aqueous solution in less than 1 minute, preferably 30 seconds. The reagent composition preferably has a moisture content of less than 10%.

The reagent composition may have at least one reagent which is unstable when alone in an aqueous solution at room temperature. The reagent composition may also comprise a plurality of reagents which may or may not react with each other when in aqueous solution at room temperature.

It is therefore an objective and advantage of the present invention to provide a dried biological reagent composition and methods of making the same.

These and still other objects and advantages of the invention will be apparent from the description below. However, this description is only of the preferred embodiments. The claims, therefore, should be looked to in order to assess the whole scope of the invention.

DESCRIPTION OF THE DRAWINGS

FIG. 8 shows Ct values and PCR efficiency for the above mentioned four reactions in duplicates. Both the Ct values and PCR efficiency values of the current format and the puRe Taq RTG beads are comparable at 40° C. and room temperature.

DETAILED DESCRIPTION OF THE INVENTION

Biological Reagents

Figure 1:
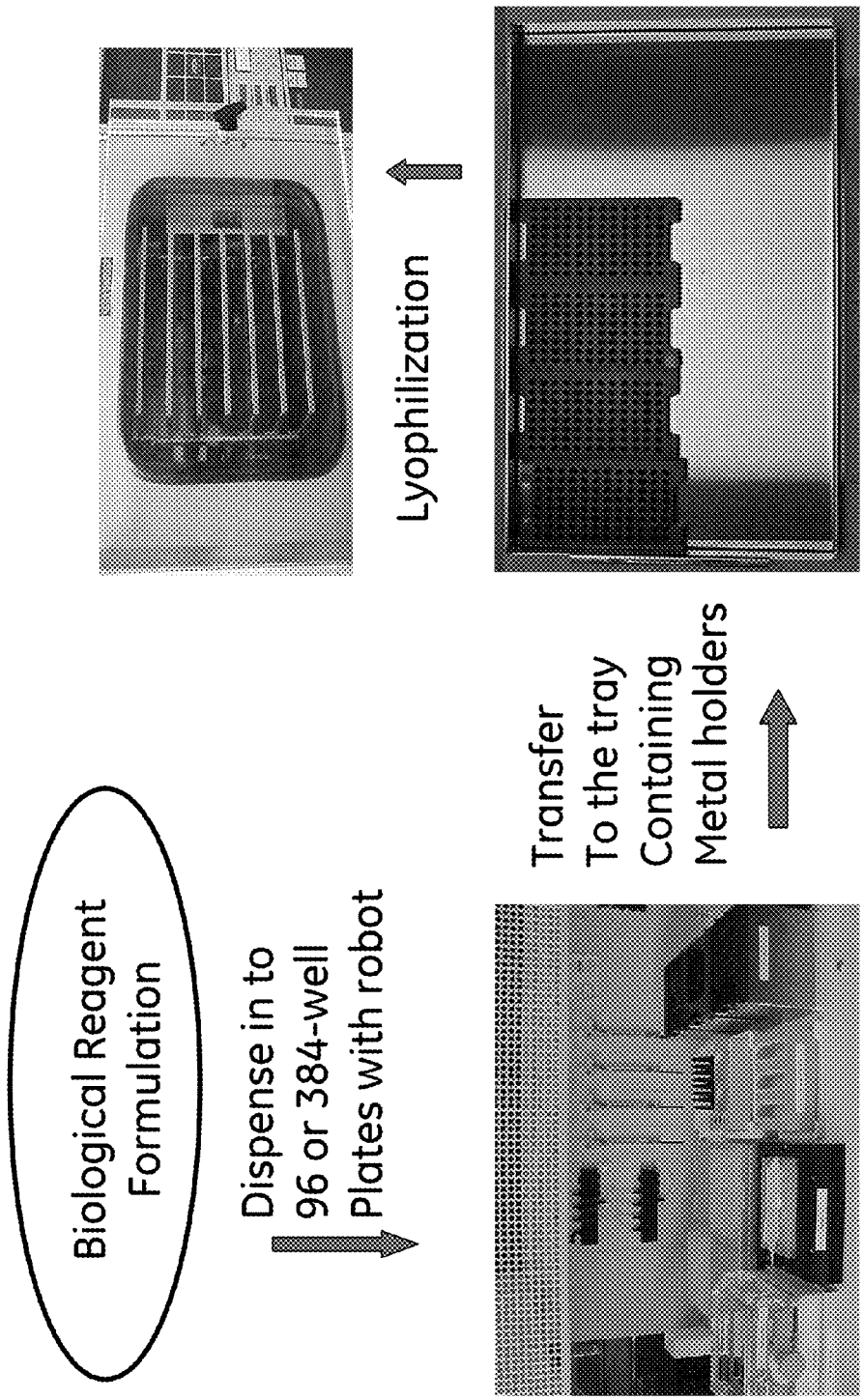
FIG. 1 shows a process work-flow of the method for making a dried reagent preparation according to an embodiment of the invention.

Many biological reagents are suitable for storage by the method of the present invention. The biological reagent compositions of the present invention are particularly suitable for performing a wide variety of analytical procedures which are beneficially or necessarily performed on blood plasma or diluted plasma. The analytical procedures will generally require that the blood plasma be combined with one or more reagent spheres so that some optically detectable change occurs in the plasma which may be related to measurement of a particular component or characteristic of the plasma. Preferably, the plasma will undergo a reaction or other change which results in a changing color, fluorescence, luminescence or the like, which may be measured by conventional spectrophotometers, fluorometers, light detectors, etc. In some cases, immunoassays and other specific binding assays may be performed.

A still further category of biological reagents to which the present invention is applicable is protein and peptides, including derivatives thereof such as glycoproteins. Such proteins and peptides may be any of: enzymes, transport proteins (for example hemoglobin, immunoglobulins, hormones, blood clotting factors and pharmacologically active proteins or peptides).

Another category of biological reagents to which the invention is applicable comprises nucleosides, nucleotides (such as deoxynucleotides, ribonucleotides and dideoxynucleotides), dinucleotides, oligonucleotides and also enzyme cofactors, whether or not these are nucleotides. Enzyme substrates in general are also biological reagents to which the invention may be applied.

The biological reagent for stabilization in storage may be isolated from a natural source, animal, plant, fungal or bacterial, or may be produced by and isolated from cells grown by fermentation and artificial culture. Such cells may or may not be genetically transformed cells.

Another development of this invention is to store more than one reagent of a reacting system in a glass reagent sphere. This can be useful for materials which will be required to be used together in, for example, an assay or a diagnostic kit.

Storing the reagents in a single glassy preparation provides them in a convenient form for eventual use. For instance, if an assay requires a combination of a substrate or cofactor and an enzyme, two or all three could be stored in a glassy reagent sphere in the required concentration ratio and be ready for use in the assay.

If multiple reagents are stored, they may be mixed together in an aqueous emulsion and then incorporated together into a glass. Alternatively, they may be incorporated individually into separate glasses which are then mixed together.

When multiple reagents are stored as a single composition (which may be two glasses mixed together) one or more of the reagents may be a protein, peptide, nucleoside, nucleotide, or enzyme cofactor. It is also possible that the reagents may be simpler species. For instance, a standard assay procedure may require pyruvate and NADH to be present together. Both can be stored alone with acceptable stability. However, when brought together in an aqueous solution they begin to react. If put together in required proportions in the glassy reagent sphere, they do not react and the glass can be stored. By react we mean any biochemical reaction.

The preferred biological reagents of the present invention are enzymes and cofactors that provide a reagent system to detect, amplify, modify or sequence nucleic acids. Such enzymes include but are not limited to DNA polymerases (e.g. Klenow), T7 DNA polymerase or various thermostable DNA polymerases such as Taq DNA polymerase; AMV or murine reverse transcriptase, T4 DNA ligase, T7, T3, SP6 RNA polymerase, Phage Phi29 DNA polymerase, and restriction enzymes. Cofactors include nucleotides, oligonucleotides, DNA, RNA, required salts for enzyme activity (e.g. magnesium, potassium and sodium), and salts required for buffer capacity. Buffer salts provide a proper pH range and aid stability. Some buffers which may be used include Tris pH 7.6-8.3.

Any potential biological reagents may be evaluated using a protocol according to Example 1, infra. Thus, suitable biological reagents are rendered stable in the reagent sphere as determined by a functionality test like that in Example 1.

Glass-Forming Filler Material

Examples of glass forming filler materials which may be used in the present invention include carbohydrates such as FICOLL™, sucrose, glucose, trehalose, melezitose, DEXTRAN™, and mannitol; proteins such BSA, gelatin, and collagen; and polymers such as PEG and polyvinyl pyrrolidone (PVP). The glass forming filler materials are preferably FICOLL™ polymer, BSA, sucrose, DEXTRAN™, or combinations thereof. A most preferred glass forming filler material for use in the present invention is FICOLL™ polymer.

Formulation

The formulation of a high viscosity mixture of biological reagent, glass forming filler material, and water is determined by an iterative process. First, one determines final as used concentrations desired of the system. The concentrations are normally stated in terms of molarity. Each biological reagent may have different formulations. Secondly, these concentrations are converted to a weight/dose basis for solids and a volume/dose basis for liquids.

Third, an initial value is chosen for the percent solids concentration of the high viscosity mixture and the desired mixture volume. A 55% solids concentration has been shown to work well. Above a 62% solids concentration the mixture is too stringy for dispensing. If an emulsion is desired, below a 52% solids concentration the mixture is too thin and dries clear and hard. If a semi-emulsion is desired, a lower limit of 10% is permissible. By "% solids" we mean (weight solids times 100) div (weight liquid plus weight solids).

The mixture will dry hard and glassy if the glass forming material is allowed to go into solution. Thus, the desired mixture is an emulsion rather than a solution. By emulsion we mean a saturated mixture such that two phases, solid and liquid, are present. For example, the present invention is a semi-emulsion of a glass forming filler material in a biological reagent/buffer solution. The presence of the solids gives the emulsion an opaque to white color. A high viscosity emulsion still forms a glass when dried, but pores are available on the surface for water to move through and speed dissolution of the dried reagent preparation. The emulsion should have a white color. If it is clear, it most likely will dry hard and glassy, and therefore, will be nonporous. By porosity we mean that the dried reagent preparation contains pockets of air bubbles which assist in the dissolution of the preparation. A preferred porosity would allow the preparation to dissolve in about 2 minutes or less.

Another version of the invention provides a mixture of glass forming filler material and a biological reagent/buffer solution which is characterized as being a semi-emulsion. By this we mean a mixture having at least some properties of an emulsion. The semi-emulsion of the present invention may be formed by using the above iterative process to arrive at a solids concentration of about 10% to about 50%. The semi-emulsion can then be dispensed and dried to form the dried reagent preparation.

Fourth, one calculates the number of doses that can be made using the grams of glass forming material per dose from the second step.

Fifth, using the number of doses and the weight per dose ratios from the second step, one determines the weights in volumes of the other components. Finally, using the weights and volumes determined in the fifth step, one calculates the percent solids of the final mixture. If the final percent solids of the mixture are out of the desired range, one repeats the third through sixth steps with another initial value until the final value is in the correct range.

Any potential glass forming material may be evaluated using a protocol according to the iterative process described above. Thus, a suitable glass forming material produces a reagent preparation having an acceptable hardness, size, shape, $T_g$, porosity, solubility, and stability.

Multi-Well Containers

Examples of multi-well containers for making the dried reagent preparation include a polystyrene plate, a silica mould, or the like. Preferably, the multi-well plate is one that has a standard dimension and layout that enables to use standard thermal cyclers for applications like PCR.

Generally, the multi-well containers comprise two regions, a well field and a border. The border can be of any dimension, shape, or thickness, but preferably forms a multi-well platform with outer dimensions that are similar to those of a standard 96- or 384-well commercial microtiter plate, whose dimensions are approximately 85.5 mm in width by 127.75 mm in length.

Typically, the plate contains a number of hollows arranged in a grid. These hollows are known as wells and act as reaction vessels for individual reactions, or storage containers for individual samples. Wells will be arranged in two-dimensional linear arrays on the multi-well platform. However, the wells can be provided in any type of array, such as geometric or non-geometric arrays. The number of wells can be a multiple of 96 within these ranges, preferably the square of an integer multiplied by 96.

Wells in the commercial plates are typically designed with standard spacing. A 96-well plate has twelve columns and eight rows with 9 mm spacing between the centers of adjacent wells. A 384-well plate has twenty-four columns and sixteen rows with 4.5 mm spacing between the centers of adjacent wells. A 1536-well plate has forty-eight columns and thirty-two rows with 2.25 mm spacing between the centers of adjacent wells. Microtiter plates constituting one half of the above format are also in use. Also available are strips of wells that have similar spacing between the centers of adjacent wells. Multi-well containers having these dimensions can be compatible with robotics and instrumentation, such as multi-well platform translocators and readers as they are known in the art.

The materials for manufacturing the multi-well platform will typically be polymeric, since these materials lend themselves to mass manufacturing techniques. Preferably, polymers are selected that are known to have low fluorescence or other properties. Various methods in the art can be used to confirm that selected polymers possess the desired properties. Polymeric materials can particularly facilitate plate manufacture by molding methods known in the art and developed in the future, such as insert or injection molding.

An alternative to the polymeric plates are silica moulds in a 96-well and 384-well formats. As shown in the Examples infra, a 96-well perforated silica molded plate can be used for dispensing and lyophilizing the reagents. The advantage here is the dried reagents should be easily removed from the mould after lyophilization.

Mixing and Dispensing

A typical formulation (using DNA labeling formulation as the example) is made as follows:

All reagents used are typically autoclaved or filter sterilized (preferably a 0.25 μm filter) before use. Formulations are made and stored on ice until dispensed. For 200 mls (enough for 20,000 single dose preparation) of a DNA labeling formulation, 15 g each of FICOLL™ 400 and FICOLL™ 70 and 20 g melezitose are added to approximately 90 ml of sterile water and mixed on a stir plate until dissolved.

50 ml of a 20× concentrated DNA labeling buffer (200 mM Tris pH 7.5, 200 mM $MgCl_2$ 1M NaCl) is added along with 10 mls of a 10 mg/ml BSA solution. One ml each of 100 mM ATP, GTP, and TTP are added. Once all the reagents are in solution the formulation is stored on ice or under refrigeration until it is to be used for dispensing. Just before use, 400 Ku of Klenow fragment DNA polymerase is added (minimum concentration of stock should be 100 Ku/ml in order to keep the glycerol concentration below 1% in the final preparation). Also just before use, 1200 A 260 Units of $d(N)_9$ primer is added. Before adding to the formulation, the primer should be heated at 65° C. for 7 minutes and quickly cooled on ice. After addition of the enzyme and primer, the final volume should be brought to 200 ml with sterile water. The density of the final solution will be 1.14 g/ml.

The final volume per dose dispensed of the reagent homogeneous solution is often small, such as 5-30 μl, preferably 10 μl, to allow a working volume of 10-100 μl when the reagent preparation is dissolved in a working solution.

A predetermined amount of homogeneous solution is dispensed into each well of a multi-well container, typically using a liquid dispensing robot (96 well/384 well pins). The solution is dispensed in a volume ranging from 4 μl to 20 μl but preferably 10 μl.

Driving Process

The sample dispensed can be dried by freeze-drying or lyophilization. A suitable drying program produces a reagent preparation having an acceptable hardness, size, shape, $T_g$, porosity, solubility, and stability.

A typical successful freeze-drying profile is shown below in Table 1.

TABLE 1

| Temperature (° C.) | Vacuum (mTorr) | Time (min.) | Comment |
|---|---|---|---|
| −46 | atmosphere | 60 | hold |
| −46 | 40 | 600 | hold |
| −36 | 40 | 250 | ramp |
| −36 | 40 | 300 | hold |
| 0 | 40 | 400 | ramp |
| 0 | 40 | 300 | hold |
| 28 | 40 | 233 | ramp |
| 28 | 40 | 240 | hold |

Figure 4:
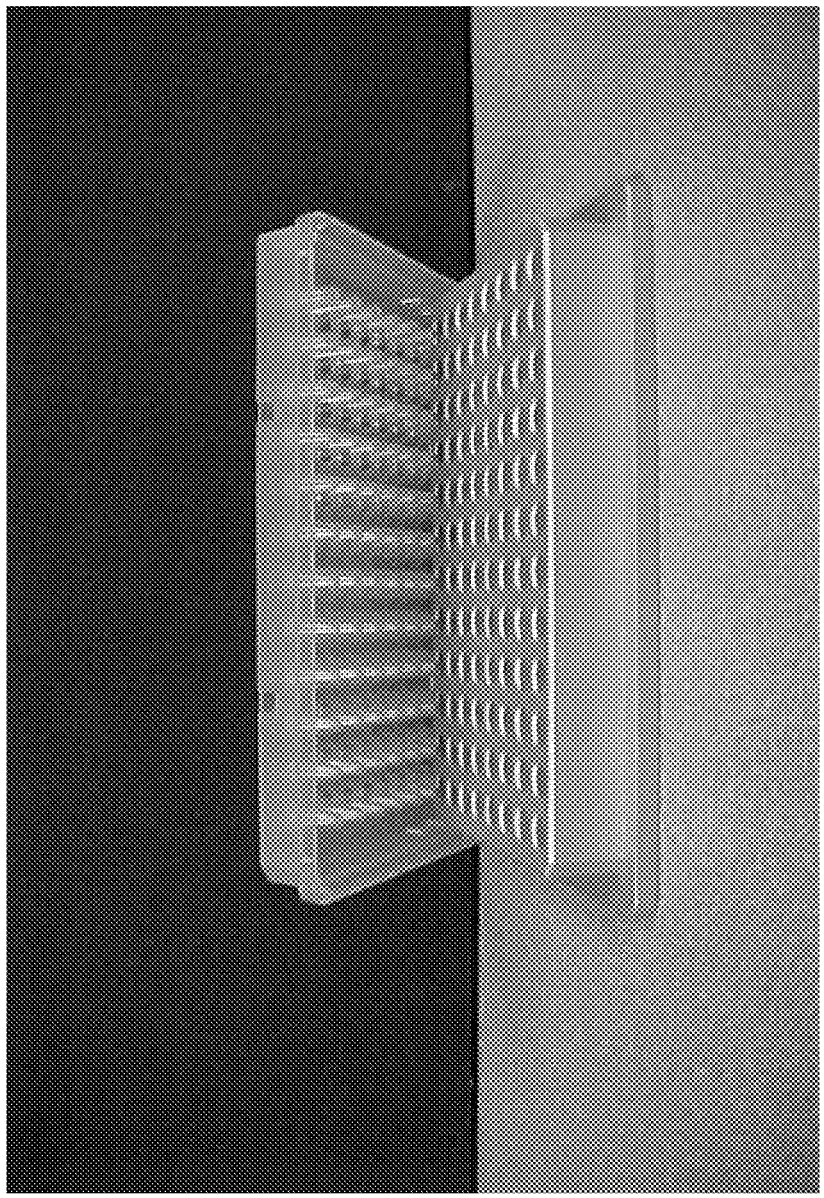
FIG. 4 shows a 96-well PCR plate containing PCR formulation goes into a metal holder before lyophilizing.
Figure 5:
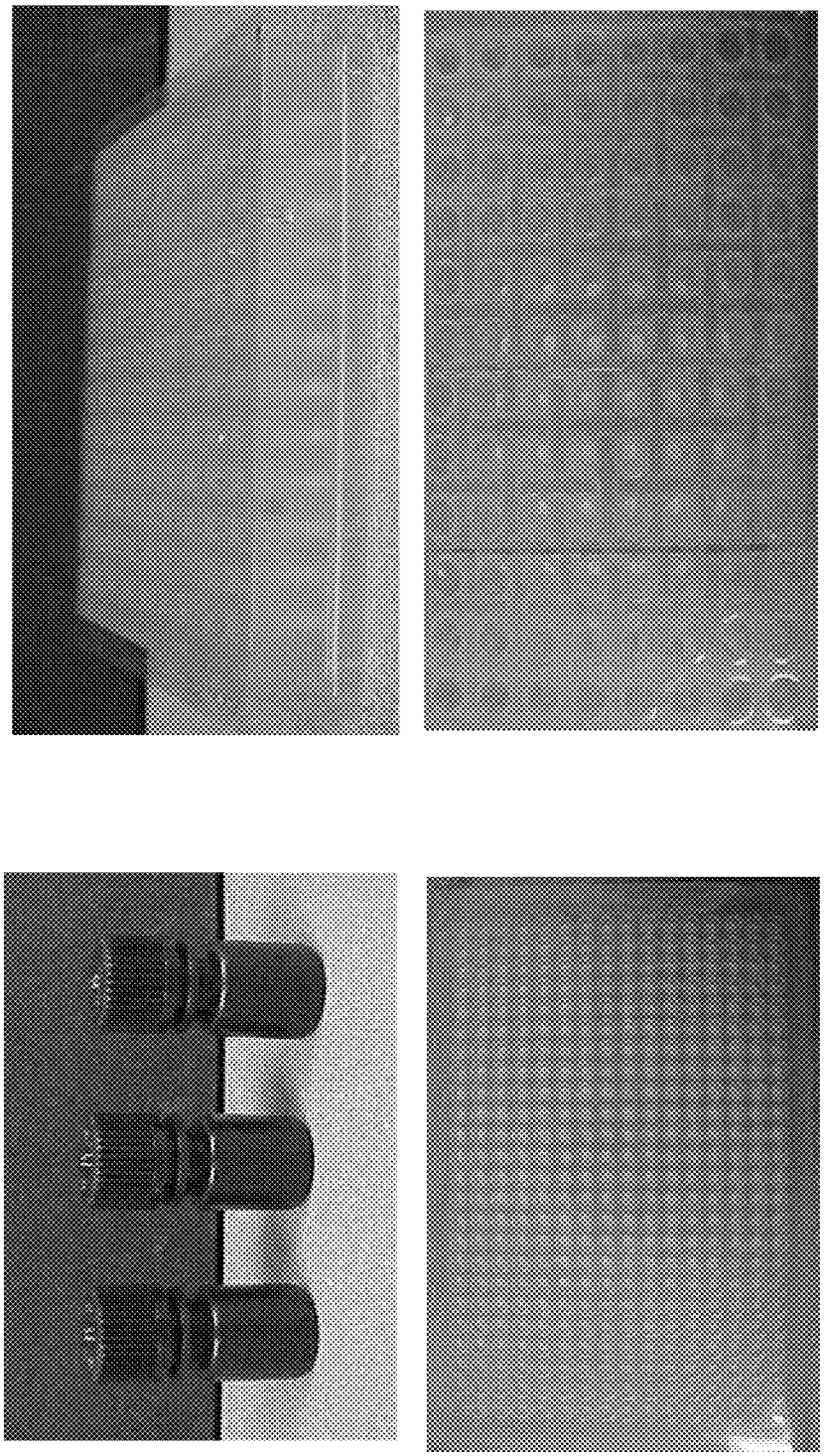
FIG. 5 shows room temperature stable PCR reagents made according to an embodiment of the invention in different formats. Top left: dried PCR mix in a bottle. Top right: dried PCR mix in 96-well plate. Bottom left: dried PCR mix in 384-well plate. Bottom right: dried PCR mix in 96-well perforated plate.

A preferred method of drying is by way of lyophilization. The dispensed reagents are successfully dried in a 96- or 384-well polystyrene plate. Surprisingly, when the polystyrene thin-walled plate was placed onto and in direct contact with a fitted metal plate holder, the drying process works better and no foam or flakes of the dried reagent observed compared to the plates dried without metal holders (FIGS. 1 and 4). Direct contact of the outside wall of a polystyrene well (tube) with the metal well of the metal plate holder indirectly enhances the metal shelf contact area, which in turn achieves a better heat transfer to the samples. A silica mould, on the other hand, has a thick wall and flat bottom for each well, and the lyophilization process in a silica mould works reasonably well without the use of a metal holder. This is probably due to the better contact of the mould with the freeze-dryer shelf and the heat transfer properties of the silica. A preferred lyophilization profile is shown below in Tables 2. Note that the samples are frozen in the freeze-drier for 1 hour at −46° C. before running the following program.

TABLE 2

| Temperature (° C.) | Vacuum (mTorr) | Time (min.) | Comment |
|---|---|---|---|
| −46 | 100 | 600 | hold |
| −36 | 100 | 250 | ramp |
| −36 | 100 | 300 | hold |
| 0 | 100 | 400 | ramp |
| 0 | 100 | 300 | hold |
| 28 | 100 | 233 | ramp |
| 28 | 100 | 360 | hold |
| Post Heat: | | | |
| 28 | 100 | 2000 | hold |

Storage

We successfully prepared stable biological reagents in tablet, cylinder and cube formats in polystyrene and silica based plates or moulds. Our technology allows the stabilization of temperature sensitive protein and nucleic acid molecules into single-dose format, stable at ambient temperatures. The single-dose format (bead or cake) can contain the pre-dispensed buffer, salt, detergent and nucleotide, etc. needed for the specific assay, in which the molecules are used. These enzymes and combinations can be used for a variety of molecular biology applications, including but not limited to PCR, RT-PCR, real time PCR, whole genome amplification, in vitro transcription and cDNA synthesis applications.

Our method eliminated the need to freeze drop the reagent mix into liquid nitrogen or onto a cold surface, yet the dried reagents maintain good structural integrity. The method has fewer steps in the manufacturing process. The dried reagent preparations can be stored in the plates or moulds directly when properly sealed and this significantly reduces the manufacturing and packaging costs. Alternatively, the dried reagents can be removed from silica moulds as tablets and from polyfiltronics 96-well plates as cubes and stored in sealed containers, i.e. capped bottles.

Sealing of the plate or mould can be achieved by: lid, tape, heat activated tape etc. In one embodiment of the invention, sealing of the plates is achieved by heat activation sealing using AbGene's Thermo-Seal and Easy-Peel sheets.

A reagent preparation of the present invention is room temperature stable. By "room temperature stable," we mean that the preparation can be stored at 22° C. for greater than 6 months with less than 20% loss of enzymatic activity as compared to the activity measured after the reagents are first dried.

A reagent preparation of the present invention has a glass transition temperature ($T_g$) of at least 10° C. A typical $T_g$ of the reagent preparation is 40° C. A $T_g$ of at least 40° C. will guarantee stability at room temperature (22° C.). A preferred $T_g$ is 45° C. The glass transition temperature is the temperature above which the viscosity of a glassy material drops rapidly and the glassy material turns into a rubber, then into a deformable plastic which at even higher temperatures turns into a fluid.

The glass transition temperature is used as an important indicator of stability of the preparation. At temperatures below or near the $T_g$ the sample remains as a stable glass. As the temperature rises above the $T_g$, the sample becomes a rubber and is less stable. The $T_g$ is measured using differential scanning calorimetry. 2-5 mg (1-2 spheres crushed) of sample are put into an aluminum pan. The $T_g$ of the sample is determined by subjecting the sample to a controlled temperature program from 0° C. to 100° C. at a rate of 10° C./min. The heat flow to and from the sample is measured and expressed as a shift in the baseline. The $T_g$ is expressed as the temperature at the midpoint of this baseline shift.

A typical porosity will allow dissolution of the sphere in 20 μl of water in 1 minute or less. A preferred porosity will allow dissolution in 30 seconds or less.

Our method of making glassified biological reagent preparation offers several advantages. The manufacturing process is greatly simplified. The reagent mixture is dispensed directly into wells of a multi-well plate, which has a standard format as the commercial microtiter plate. This eliminated the need to freeze the reagent droplets in liquid nitrogen or on a cold surface. The dispensed mixture is then frozen, lyophilized in the well, and can be stored in the well too. This eliminated the need of moving the beads or the cakes from a drying pan into a storage container. Because the dried composition can be stored in the multi-well plate, the composition can be used in a subsequent workflow that is automated. Robotic systems can be used for processing the plates.

In addition, the compositions made are stable at ambient temperature. This saves cost on shipping (no dry-ice shipping), eliminates the need for freezer storage and shortens the reagent preparation time (no thawing). It offers convenience for the subsequent user. Most of the assay-related components could be pre-dispensed and stabilized into the single dose format. It saves the user time and plastic consumable costs for preparing the reagents master mix. It also offers increased reproducibility and reliability, as it reduced risk of contamination and errors. The composition is prepared with pre-dispensed reactions. This minimizes sample handling and pipetting steps, thus reducing the risk of contamination and pipetting errors by the user.

EXAMPLES

The present examples are provided for illustrative purposes only, and should not be construed as limiting the scope of the present invention as defined by the appended claims. All references given below and elsewhere in the present specification are hereby included herein by reference.

Example 1

Preparation of Dried PCR Mixture in a 384-Well Polystyrene Plate

The biological reagent formulation, in this case, a reagent mixture for PCR is prepared according to standard protocol. In short, the formulation of the 10 μl sphere contains 25 mM Tris-HCl (pH 9.0 at room temperature), 125 mM KCl, 3.75 mM MgCl2, 0.5 mM dNTP's, 0.6 mg/ml BSA, 3.5 units of rTaq DNA polymerase, and the glass-forming filler material comprising synthetic polymers FICOLL™ 400 (6.25%), FICOLL™ 70 (6.25%) and the secondary carbohydrate Melezitose (10%). All reagents are typically autoclaved or filter sterilized before use. Formulations are made and stored on ice until mixed and dispensed into polystyrene plates or silica moulds. Final formulation consists of glass forming filler material, BSA, dNTPs, and rTaq DNA polymerase and salts as described above.

The final volume per dose of the reagent homogeneous solution was 10 μl. This allowed a working volume for PCR of 25 μl. The reagent was dispensed using an automatic pipette into a 384-well polystyrene plate.

The 384-well plate was placed on top of the pre-cooled (−46° C.) Vertis freeze-dryer shelf for about 60 minutes to freeze the reagents. The frozen reagents were then subjected to the primary and subsequent secondary drying processes, according to the process described in Table 2 supra.

The plate containing the dried reagents was stored in a re-sealable pouch containing desiccant as an integrated package by simply covering the plate with an adhesive cover or lid or a thermo seal. Alternatively, the dried reagents were removed from the plate as dried reagent tablets or cubes and were stored in a bottle and the bottles were stored in re-sealable pouch containing desiccant.

Stability of the dried reagent composition was tested by real-time PCR amplification of Lambda DNA and comparing the amplification profile with that of commercial product (puRe Taq RTG beads; GE Healthcare). The primers used for the testing are SEQ ID NO: 1 (5'-GGT TAT CGA AAT CAG CCA CAG CGC C-3') and SEQ ID NO: 2 (5'-GAT GAG TTC GTG TCC GTA CAA CTG G-3'). The real-time PCR amplification results are shown in FIG. 2.

Figure 2:
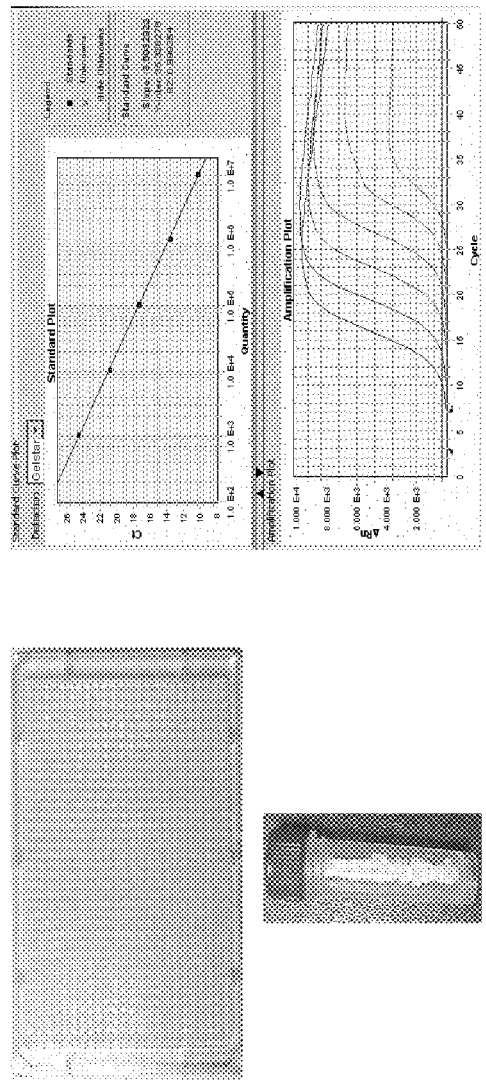
FIG. 2 shows from the top left: a 384-well polystyrene plate that is used in the method of making a dried reagent preparation according to an embodiment of the invention; top right: standard curve showing different amounts of lambda DNA as template with starting concentration of 10 million copies to 1000 copies including a no template control; bottom left: dried reagent preparation cake/cube made from the 384-well polystyrene plate, stored in a plastic bottle; bottom right: the amplification plot showing that the dried reagent preparation is successfully used in the Lambda DNA real-time qPCR amplification reactions.

In FIG. 2, a 384-well polystyrene plate is shown on the upper left side, which was used for making the dried reagent composition. The dried reagent tablets were stored in a plastic bottle (bottom left side) and stored at room temperature for about a week in a resalable pouch containing the desiccant. A 384-well plate containing the dried reagents is shown on the upper left side and is covered with the adhesive seal. The standard curve of different dilutions of lambda DNA template is shown on the upper right side. The real-time amplification curves of different dilutions of lambda DNA is shown on the bottom right side. In conclusion, the success in real-time PCR amplification reactions proof that the dried reagent composition is stable.

Example 2

Preparation of Dried PCR Mixture in a 96-Well Silica Mould

Figure 3:
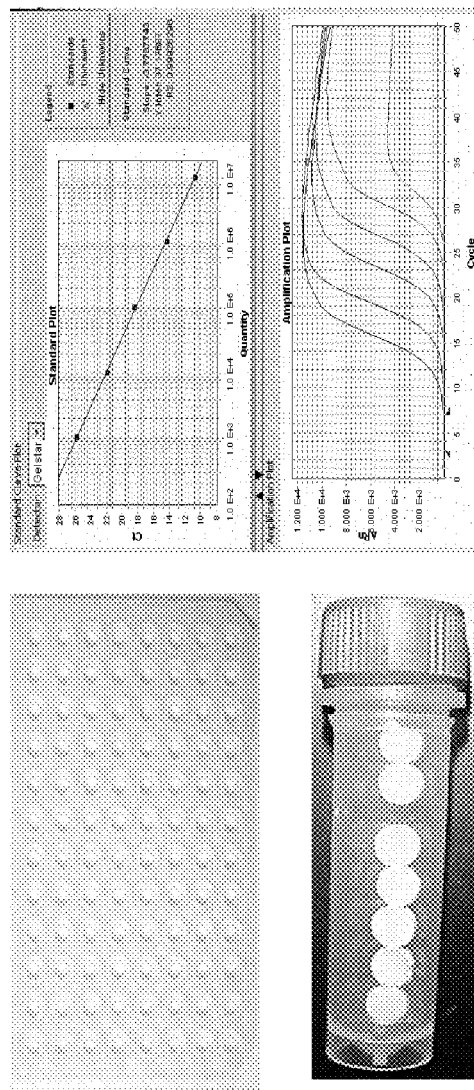
FIG. 3 shows from the top left: a 96-well silica mould that is used in the method of making a dried reagent preparation according to an embodiment of the invention; top right: standard curve showing different amounts of lambda DNA as template with starting concentration of 10 million copies to 1000 copies including a no template control; bottom left: dried reagent tablets made from the 96-well silica mould, stored in a plastic bottle; bottom right: the amplification plot showing that the dried reagent preparation is successfully used in the Lambda DNA real-time qPCR amplification reactions.

The biological reagent formulation and the glass-forming filler material are prepared and mixed together according to Example 1. About 20 μl reagent mixture was dispensed using an automatic pipette into a 96-well silica mould (FIG. 3, upper left side). The silica mould was placed in a pre-cooled (−46° C.) Vertis freeze-dryer for about 60 minutes to freeze the reagents. The frozen reagents were then subjected to the primary and subsequent secondary drying processes, according to the process described in Table 2 supra.

The dried reagents could be stored in the mould as an integrated package by simply covering the mould with an adhesive seal and by placing the plate in aluminum pouch containing desiccant. Alternatively, the dried reagents were removed from the mould as dried reagent cakes and were stored in a bottle containing desiccant.

Stability of the dried reagent composition was tested by real-time PCR amplification of Lambda DNA according to Example 1, and comparing the amplification profile with that of commercial product (puRe Taq RTG beads; GE Healthcare). The results are shown in FIG. 3.

In FIG. 3, a 96-well silica mould is shown on the upper left side, which is used for making the dried reagent composition. The dried reagent cubes were stored in a plastic bottle (bottom left side) for a week in a re-sealable pouch containing the desiccant before performing the lambda DNA functional test. The standard curve of different dilutions of lambda DNA template is shown on the upper right side. The real-time PCR amplification plots of the different dilutions of lambda is shown on the bottom right side. In conclusion, the success in real-time PCR amplification reactions proof that the dried reagent composition is stable.

Example 3

Preparation of Dried PCR Mixture in a 96-Well Polystyrene Plate

The biological reagent formulation and the glass-forming filler material were prepared and mixed together according to Example 1. 10 µl reagent mixture was dispensed using an liquid dispensing robot (FIG. 1, bottom left side). The 96-well plate was placed on a 96-well metal holder (FIG. 4). The 96-well plate with the metal holder was placed on top of the pre-cooled (−46° C.) Vertis freeze-dryer shelf for about 60 minutes to freeze the reagents. The frozen reagents were then subjected to the primary and subsequent secondary drying processes, according to the process described in Table 2 supra.

The dried reagents could be stored in the 96-well plate as an integrated package by simply covering the plate with an adhesive seal or a lid or a thermoseal with the help of a heat sealer. Lambda DNA real-time PCR functional test was performed with the freshly prepared "wet" formulation and the dried reagents along with puRe Taq RTG beads. The sealed plates were stored at room temperature or in a 40° C. incubator for 8 days in a pouch containing desiccant. Stability of the dried reagent composition was tested by real-time PCR amplification of Lambda DNA (according to Example 1) and comparing the amplification profile with that of commercial product (puRe Taq RTG beads; GE Healthcare). The results are shown in FIGS. 6, 7 and 8.

Figure 6:
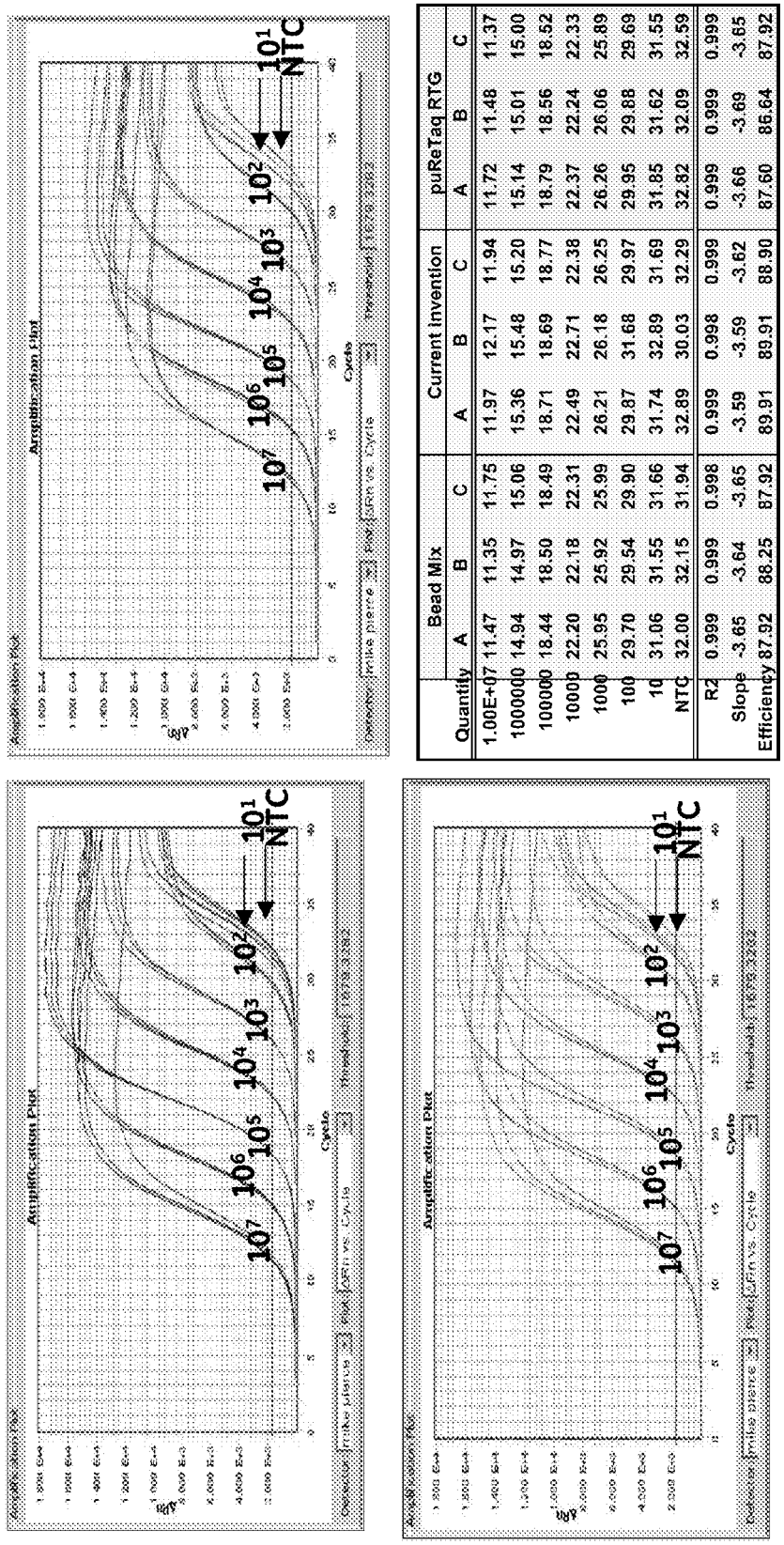
FIG. 6 shows stability of dried PCR reagents made according to an embodiment of the invention. Dried PCR mix was used for qPCR of Lambda DNA. Similar performance was noticed with (1) the 'wet' formulation bead mix (upper left), (2) dried cakes made using current protocol (upper right), and (3) PURE TAQ READY-TO-GO™ (RTG) PCR beads from GE Healthcare (lower left). Lower right: Ct values and PCR efficiency for the above mentioned three reactions in triplicates. Both the Ct values and PCR efficiency values of the new format and the puRe Taq RTG beads are comparable.

FIG. 6 shows Lambda qPCR with 96-well dried PCR cakes and comparison with the 'wet' formulation and the puRe Taq RTG beads. The figure shows stability of dried PCR reagents made according to an embodiment of the invention. Real-time PCR amplifications were performed with different concentrations of Lambda DNA starting from 10 million copies to 10 copies as template along with a no template control. Similar performance in terms of Ct values and PCR efficiency (bottom left table) was noticed with current format (upper right), puRe Taq RTG beads (lower left) and the 'wet' formulation (upper left).

Figure 7:
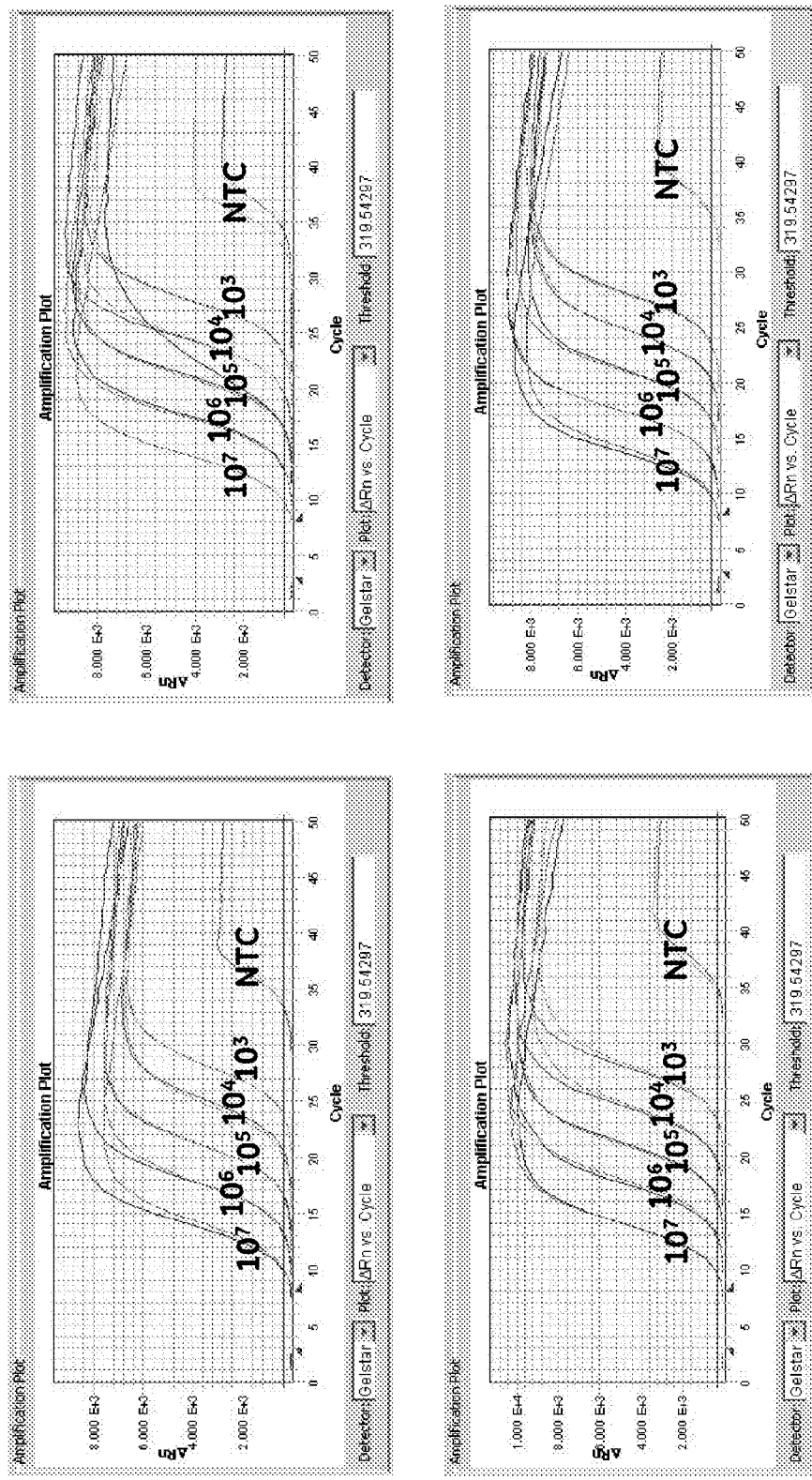
FIG. 7 shows stability of dried PCR reagents made according to an embodiment of the invention. Dried PCR mix was stored at 40° C. and Room Temperature (RT) for 8 days. The dried reagents were used for qPCR of Lambda DNA, with similar performance. Top left: dried PCR reagent cakes stored at RT. Top right: dried PCR reagent cakes stored at 40° C. Bottom left: puRe Taq RTG beads (GE Healthcare) stored at RT. Bottom right: puRe Taq RTG beads stored at 40° C.

FIG. 7 shows stability of dried PCR reagents made according to an embodiment of the invention. Dried PCR mix was stored at 40° C. or Room Temperature (RT) for 8 days, then used for qPCR of Lambda DNA. The reagent made according to present invention achieved similar performance, as compared to commercial puRe Taq RTG bead. Top left: dried PCR reagent cakes stored at RT. Top right: dried PCR reagent cakes stored at 40° C. Bottom left: puRe Taq RTG beads stored at RT. Bottom right: puRe Taq RTG beads stored at 4°° C. FIG. 8 shows the Ct values and the PCR efficiency for the current format reagents and the puRe Taq RTG beads at room temperature and 40° C.

Example 4

Preparation of Dried Reagents for Real-Time PCR Assay

Real-time PCR is become an increasingly popular assay platform for gene expression analysis. One method for detection of amplified product in real time PCR utilizes a dual labelled single stranded (ss) DNA probe that is homologous to a specific portion of the template. The fluorescent modifications on this probe serve as a reporter (FAM) and quencher (TAMRA). In the presence of a single stranded template, the probe anneals to the template but does not emit fluorescent signal because of close proximity of the reporter dye to the quencher dye. When Taq DNA polymerase amplifies DNA from the template the 5'-3' exonuclease activity of the enzyme cleaves the labelled probe annealed to the template, releasing the quencher dye allowing for the reporter to fluoresce. The fluorescent signal is then recorded by the real time instrument.

We demonstrate here that PCR primers along with a Taq-Man probe can be lyophilized in the presence of excipients and can be used in real-time PCR without loss of function relative to reactions in which the primers and probe are not lyophilized. The formulation used to make a 2.5× concentrated formulation for assaying β-actin includes: 25 mM Tris pH 9, 125 mM KCl, 3.75 mM $MgCl_2$, 0.6 mg/ml BSA, 0.5 mM dNTPs, 0.25 U/µl rTaq, 0.05% Tween 20, 0.05% NP-40, 1.5 µM β-actin Fwd primer (SEQ ID NO: 3: 5'-TCA CCC ACA CTG TGC CCA TCT ACG A-3'), 1.5 µM β-actin Rev primer (SEQ ID NO: 4: 5'-CAG CGG AAC CGC TCA TTG CCA ATG G-3'), 1 µM β-action probe (SEQ ID NO: 8: 5'-FAM-ATG CCC-N (TAMRA) CCC CCA TGC CAT C CTG CGT p-3'), 6.25% FICOLL™ 70, 6.25% FICOLL™ 400 and 10% Melezitose.

Ten microliter aliquots of the formulation were pipetted into 96-well plate and lyophilized. Single dried cakes were rehydrated in a final volume of 25 µl with varying amounts of human genomic DNA template. Real-time PCR reactions were carried out with an ABI 7900 Fast Real Time instrument. Reactions were compared to a similar formulation as above that did not contain the primers and probe. For these latter reactions the primers and probe were added during PCR reaction set up. In addition, commercially available puRe Taq RTG beads were used as an additional control.

Figure 9:
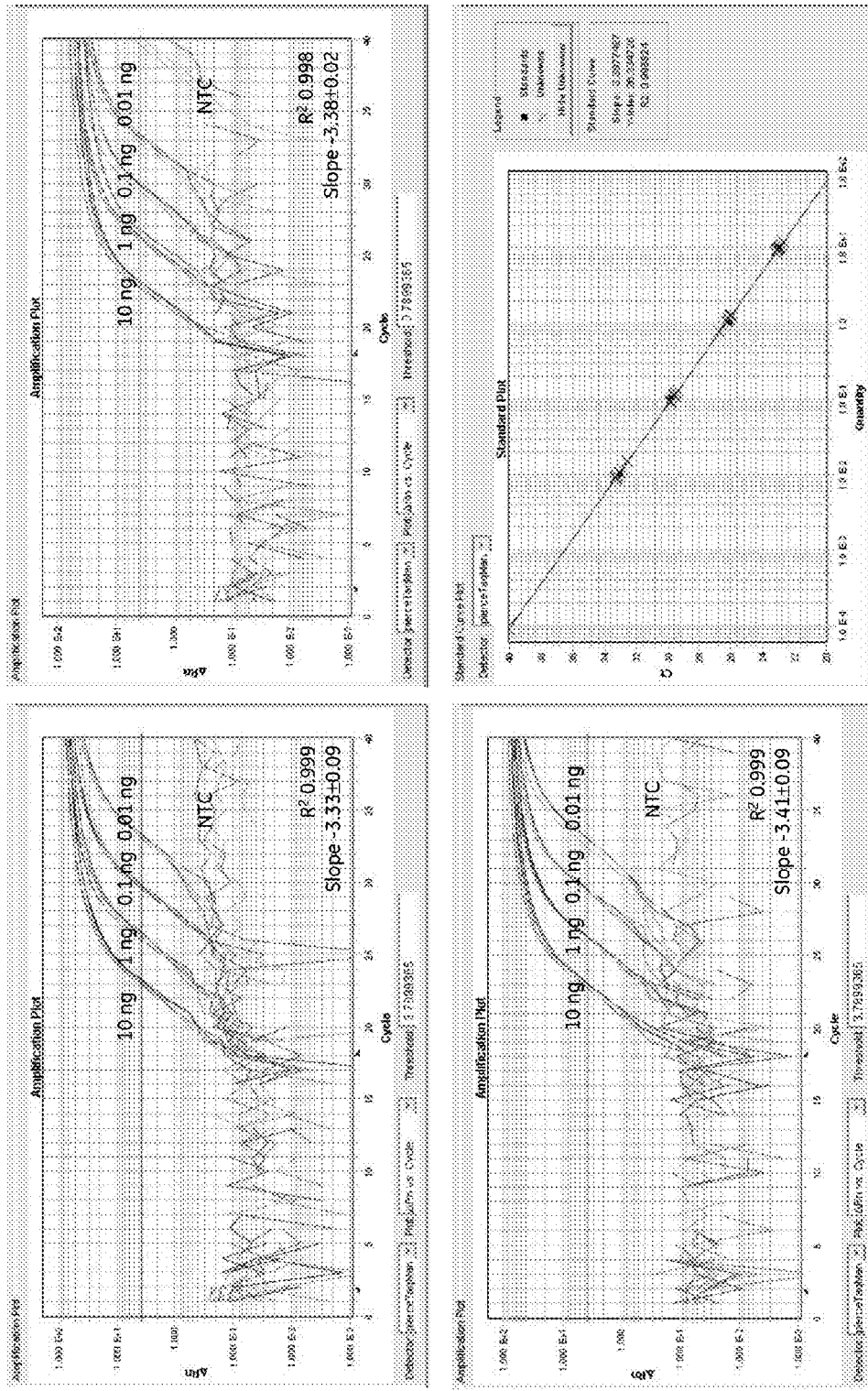
FIG. 9 shows the results of real-time PCR reactions according to one example of the invention. Upper left panel: real-time PCR using lyophilized reagents including the TaqMan primers and probe. Lower left panel: Lyophilized reagent control (TaqMan primers and probe were not lyophilized, other reagents were lyophilized as in Example 1). Upper right panel: Commercial puRe Taq RTG bead control (All the other reagents were not lyophilized). When puRe Taq RTG reactions were used to make a standard curve while treating all other reactions as unknowns the reactions with equivalent amounts of template DNA fell on the standard curve (Lower right panel, "X" denotes the "unknowns").

FIG. 9 shows the results of these reactions. Upper left panel: real-time PCR using lyophilized reagents including the TaqMan primers and probe. Lower left panel: Lyophilized reagent control (The primers and probe were not included in the lyophilized formulation, but added prior to the real-time PCT reaction). Upper right panel: Commercial puRe Taq RTG bead control (All the other reagents were not lyophilized). All reactions produced equivalent amplification profiles, $R^2$ values and slopes. When puRe Taq RTG reactions were used to make a standard curve while treating all other reactions as unknowns the reactions with equivalent amounts of template DNA fell on the standard curve (Lower right panel). Our results demonstrate that TaqMan primers and probe are amenable to RTG incorporation.

Example 5

Preparation of Dried Reagent Containing Phi29 DNA Polymerase

Phi29 DNA polymerase is widely used for whole genome amplification as well as rolling circle amplification. We lyophilized this enzyme in a formulation that enables whole genome amplification. Our analyses demonstrate that the lyophilized formulation has the same activity as the "wet" formulation in performing whole genome amplification.

GENOMIPHI™ HY (High Yield) DNA amplification kit (GE Healthcare) contains all the components necessary for whole genome amplification by isothermal stand displacement amplification. The starting material for GENOMIPHI™ reactions can be purified DNA or non-purified cell lysates. Microgram quantities of DNA can be generated from nanogram amounts of starting material in only a few hours. Typical DNA yields from a GENOMIPHI™ HY reaction are 40-50 µg per 50 µl reaction, with an average product length of greater than 10 kb. DNA replication is extremely accurate due to the proofreading 3'-5' exonuclease activity of the enzyme.

GENOMIPHI™ reaction mixture was prepared including Phi29 DNA polymerase, random hexamers, dNTPs and the GENOMIPHI™ HY reaction buffer along with the stabilizers FICOLL™ 70, FICOLL™ 400, Melezitose and BSA, as a 2× mix. Ten µl volume aliquots of the mixture were dispensed into 12-well PCR strip tubes. The dispensed products were lyophilized as a cake using VirTis freeze-drier. The dried products were stored at either room temperature or at 40° C. for 35 days. Whole genome amplification was successfully performed with these products using as low as 10 ng of human genomic DNA. This was compared with whole genome amplification using freshly prepared mixture, at time zero and after 35 days storage at RT or 40° C.

Figure 10:
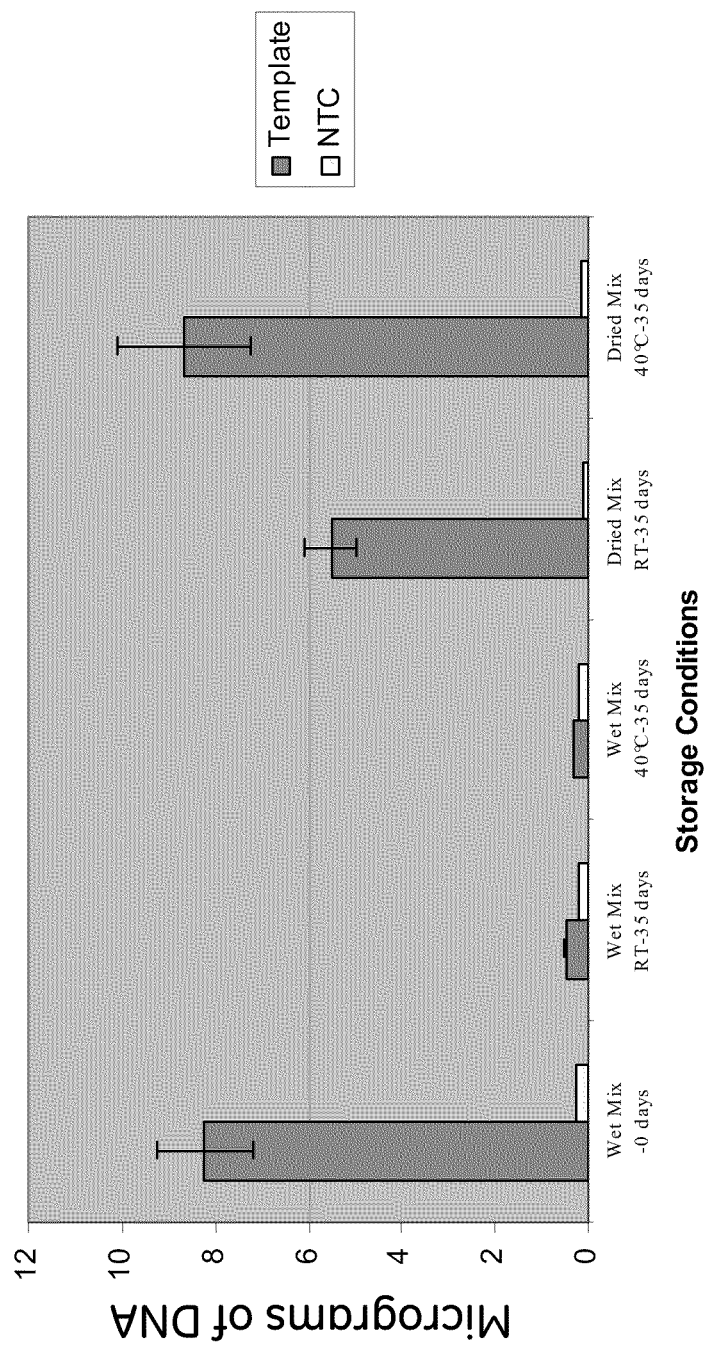
FIG. 10 shows that the Phi29 DNA polymerase is stable in the lyophilized form. Whole genome amplification assay using either lyophilized reagent or the "wet" mixture was performed. Robust amplification was detected, even with lyophilized reagent that had been stored at 40° C. for 35 days.

FIG. 10 shows the result of whole genome amplification assay using either lyophilized reagent or the "wet" mixture. Ten ng of human genomic DNA was used as template material, with a 90 minutes amplification reaction at 30° C. It was expected that greater than 4 µg of DNA should be produced in 90 minutes. Using Pico Green assay, robust amplification was detected, even with lyophilized reagent that had been stored at 40° C. for 35 days. Phi29 DNA polymerase was successfully stabilized in lyophilized format.

Example 6

Preparation of Dried Reagents for In Vitro Transcription

Transcription is a vital biological process regularly carried out by cells of all types in which RNA is made using a DNA template, by a DNA-dependent RNA polymerase, such as T7 RNA polymerase. In vitro transcription (IVT) is this same process done outside the cell in a test tube generating transcripts of choice by the end user. The resulting RNA molecules can then be used for in vitro translation of proteins, or hybridization reactions such as northern blots, southern blots, microarray analysis and microinjections.

We successfully generated lyophilized ambient temperature stable IVT reagents where all components required for RNA production minus the template were lyophilized in the presence of excipients. This greatly simplifies the IVT reaction such that the end user only needs to add template DNA and water to start the reaction The IVT formulation used for generating the lyophilized reagent includes 40 mM Tris pH 8.0, 10 mM $MgCl_2$, 4 mM Spermidine, 10 mM DTT, 50 µg/ml BSA, 10 mM NaCl, 0.5 mM ATP, 0.5 mM CTP, 0.5 mM GTP, 0.5 mM UTP, 2 U RNA Guard, 10 U T7 RNA Polymerase (GE Healthcare), 6.25% FICOLL™ 400, 6.25% FICOLL™ 70, 10% Melezitose. The prepared formulation was dispensed into 8-well strip tubes in 25 µl aliquots and lyophilized according to Example 1 and Table 2. Dried reagent cakes were tested using control DNA from the Roche SP6/T7 IVT kit. In parallel, IVT reaction was carried out using the Roche SP6/T7 IVT kit.

Figure 11:
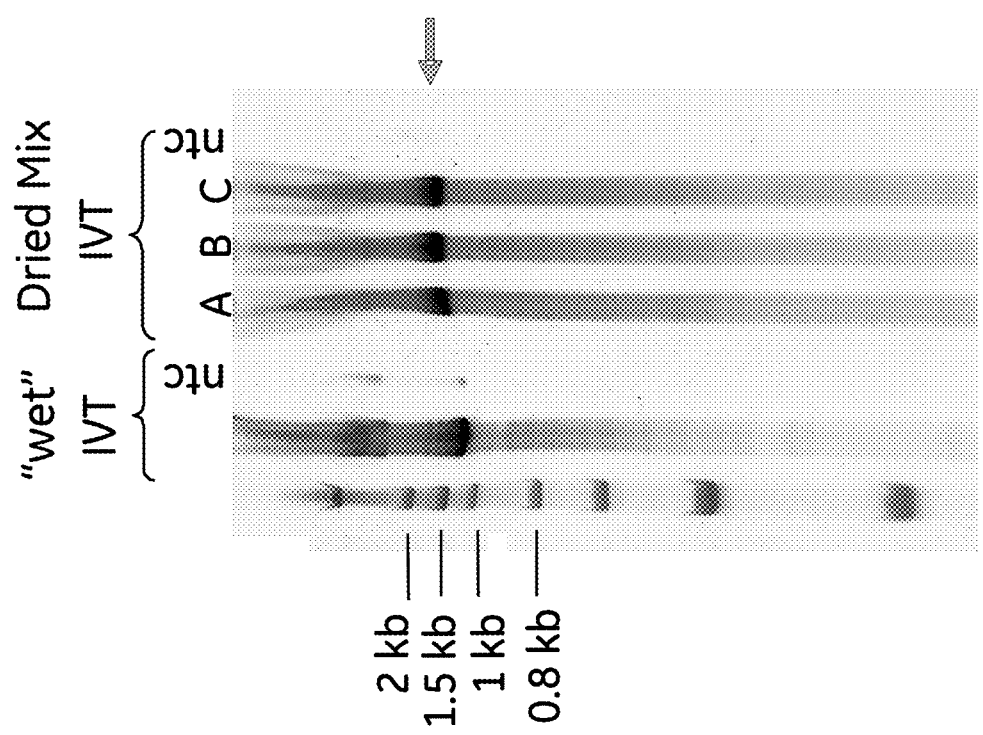
FIG. 11 shows successful transcription of a DNA template using lyophilized IVT reagent (A, B, C) as compared to conventional "wet" kit (Roche IVT). ntc: no template control.

As expected, a ~1000 base pair transcript is produced using the lyophilized reagent as well as the Roche kit (FIG. 11). Therefore, the reagents necessary for transcription was successfully lyophilized in the presence of excipients and could be rehydrated in the proper reaction volume in the presence of a DNA template to generate an RNA transcript.

While the preferred embodiment of the present invention has been shown and described, it will be obvious in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

---

What is claimed is:

1. A method of making a dried reagent preparation, comprising the steps of:
   (a) providing an aqueous solution of at least one buffered biological reagent;
   (b) mixing a glass forming filler material with the buffered reagent solution to form a mixture wherein the concentration of the filler material is sufficient to facilitate formation of a glassy, porous composition;
   (c) dispensing the mixture in the form of substantially uniform droplets into wells of a multi-well container, wherein the multi-well container is a polystyrene plate and wherein a single droplet is dispensed into each well;
   (d) placing said polystyrene plate on a metal mould wherein outside wall of each well of said multi-well polystyrene plate is in contact with a well of said metal mould;
   (e) after step d), drying the droplets in said container to form the reagent preparation; and
   (f) collecting the dried droplets into a reagent bottle for room temperature storage of the dried reagents;
   wherein the reagent preparation is water soluble and has a Tg sufficient for room temperature stability.

2. The method of claim 1, wherein said polystyrene plate is a 96-well plate.

3. The method of claim 1, wherein said polystyrene plate is a 384-well plate.

4. The method of claim 1, wherein said drying step is achieved by lyophilizing.

5. The method of claim 1, wherein said at least one buffered biological reagent is an assay mixture for a biological assay.

6. The method of claim 1, further comprising freezing said dispensed mixture prior to said drying step.

7. The method of claim 5, wherein said assay mixture includes all the reagents necessary for PCR, except amplification template and primers.

8. The method of claim 5, wherein said assay mixture includes all the reagents necessary for in vitro transcription, except the template.

9. The method of claim 5, wherein said assay mixture includes all the reagents necessary for whole genome amplification, except the template.

10. The method of claim 5, wherein said assay mixture includes all the reagents necessary for a real-time PCR assay, except the template.

11. A method of making a dried reagent preparation, comprising the steps of:
    (a) providing an aqueous solution of at least one buffered biological reagent;

(b) mixing a glass forming filler material with the buffered reagent solution to form a mixture wherein the concentration of the filler material is sufficient to facilitate formation of a glassy, porous composition;

(c) dispensing the mixture in the form of substantially uniform droplets into wells of a multi-well container, wherein the multi-well container is a polystyrene plate and wherein a single droplet is dispensed into each well;

(d) placing said polystyrene plate on a metal mould wherein outside wall of each well of said multi-well polystyrene plate is in contact with a well of said metal mould;

(e) after step d), drying the droplets in said container to form the reagent preparation; and (f) sealing the multi-well container with a sealing tape or a thermoseal for room temperature storage of the dried reagents;

wherein the reagent preparation is water soluble and has a Tg sufficient for room temperature stability.

12. The method of claim 11, wherein said sealing tape is heat-activated.

13. The method of claim 11, wherein said polystyrene plate is a 96-well plate.

14. The method of claim 11, wherein said polystyrene plate is a 384-well plate.

15. The method of claim 11, wherein said drying step is achieved by lyophilizing.

16. The method of claim 11, wherein said at least one buffered biological reagent is an assay mixture for a biological assay.

17. The method of claim 11, further comprising freezing said dispensed mixture prior to said drying step.

18. The method of claim 16, wherein said assay mixture includes all the reagents necessary for PCR, except amplification template and primers.

19. The method of claim 16, wherein said assay mixture includes all the reagents necessary for in vitro transcription, except the template.

20. The method of claim 16, wherein said assay mixture includes all the reagents necessary for whole genome amplification, except the template.

21. The method of claim 16, wherein said assay mixture includes all the reagents necessary for a real-time PCR assay, except the template.

* * * * *

SEQUENCE LISTING

```
<160> NUMBER OF SEQ ID NOS: 5

<210> SEQ ID NO 1
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 1
ggttatcgaa atcagccaca gcgcc                                           25

<210> SEQ ID NO 2
<211> LENGTH: 25
<212> TYPE: DNA
<213> ORGANISM: Artificial Sequence
<220> FEATURE:
<223> OTHER INFORMATION: Synthetic Oligonucleotide
```

```
<400> SEQUENCE: 2
gatgagttcg tgtccgtaca actgg                                          25

<210> SEQ ID NO 3
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 3
tcacccacac tgtgcccatc tacga                                          25

<210> SEQ ID NO 4
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 4
cagcggaacc gctcattgcc aatgg                                          25

<210> SEQ ID NO 5
<211> LENGTH: 26
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_signal
<222> LOCATION: (7)..(7)
<223> OTHER INFORMATION: link to tetramethylrhodamine
<220> FEATURE:
<221> NAME/KEY: misc_feature
<222> LOCATION: (7)..(7)
<223> OTHER INFORMATION: n is a, c, g, or t

<400> SEQUENCE: 5
atgcccnccc ccatgccatc ctgcgt                                         26
```